United States Patent [19]

Blott

[11] Patent Number: 4,990,144
[45] Date of Patent: Feb. 5, 1991

[54] MEDICATING IMPRESSED FILM WOUND DRESSING

[75] Inventor: Patrick L. Blott, Bishop's Stortford, United Kingdom

[73] Assignee: Smith and Nephew Associated Companies plc, England

[21] Appl. No.: 363,508

[22] Filed: Jun. 8, 1989

Related U.S. Application Data

[63] Continuation of Ser. No. 85,475, Aug. 13, 1987, abandoned.

[30] Foreign Application Priority Data

Aug. 20, 1986 [GB] United Kingdom ............... 8620227

[51] Int. Cl.$^5$ ............................................. A61F 13/02
[52] U.S. Cl. ................................... 604/304; 604/307; 128/155; 128/156
[58] Field of Search ............... 604/289, 290, 304, 307, 604/306; 128/155, 156, 114.1

[56] References Cited

U.S. PATENT DOCUMENTS

| | | | |
|---|---|---|---|
| 3,543,750 | 12/1970 | Meizanis | 128/156 |
| 3,703,897 | 11/1972 | Mack et al. | 128/156 |
| 4,413,621 | 11/1983 | McCracken et al. | 128/155 |
| 4,425,630 | 1/1981 | Lloyd et al. | 128/155 |
| 4,466,431 | 8/1984 | Tharrat et al. | 128/156 |
| 4,486,193 | 12/1984 | Shaw et al. | 604/897 |
| 4,535,020 | 8/1985 | Thomas et al. | 128/156 |
| 4,649,909 | 3/1987 | Thompson | 128/156 |
| 4,699,792 | 10/1987 | Nick et al. | 128/156 |
| 4,822,617 | 4/1989 | Panoz | 604/304 |

Primary Examiner—C. Fred Rosenbaum
Assistant Examiner—Anthony Gutowski
Attorney, Agent, or Firm—Jacobs & Jacobs

[57] ABSTRACT

A non-adherent wound dressing comprising a film which contains depressions over the wound contacting area of the dressing is described. The depressions contain a viscous pharmaceutical composition which is suitable for topical application to the skin and which preferably contains from 1 to 12.5% by weight of antibacterial agent. In a preferred form of the dressing each depression has an aperture at its apex whereby transmission of wound exudate through the dressing to an absorbent placed on the non-wound contacting surface of the dressing is permitted while at the same time the pharmaceutical composition may release its medicament to the environment of the wound.

26 Claims, 2 Drawing Sheets

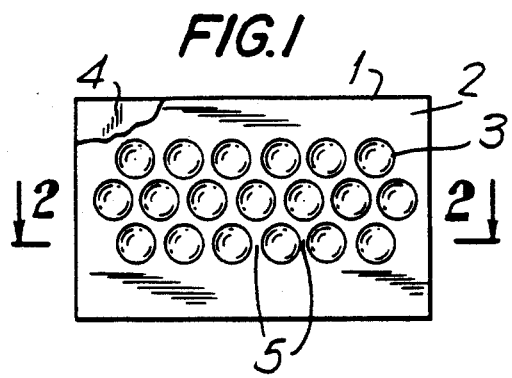
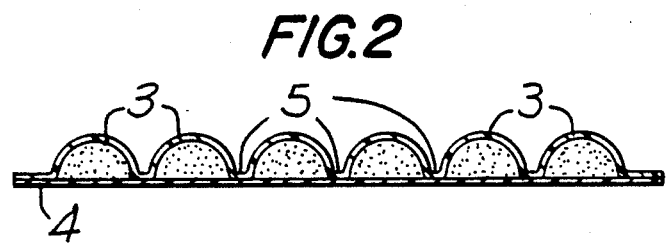
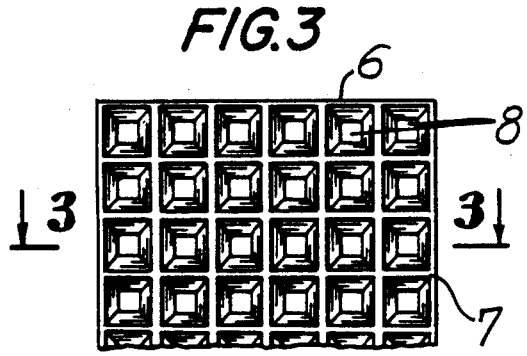
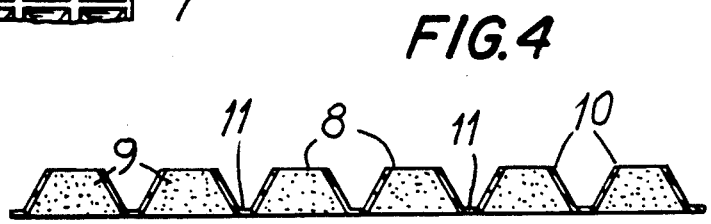
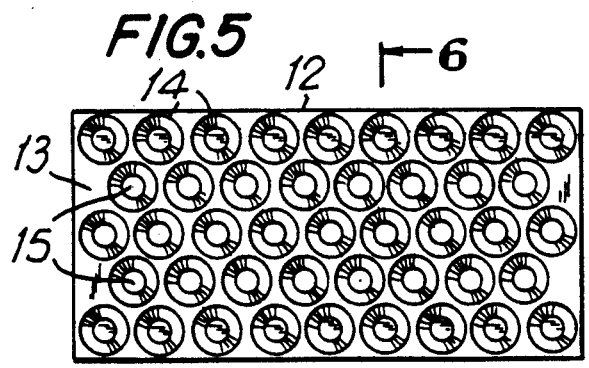
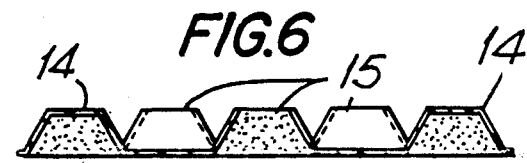

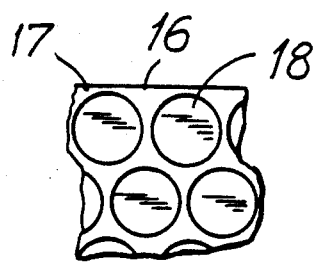
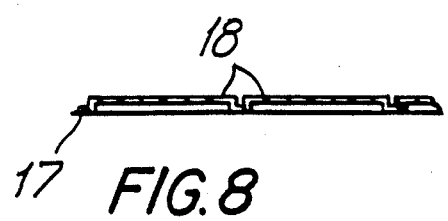
FIG.7  FIG.8
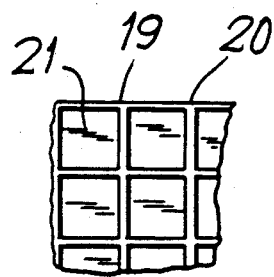
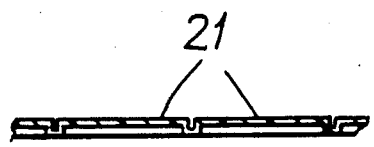
FIG.9  FIG.10
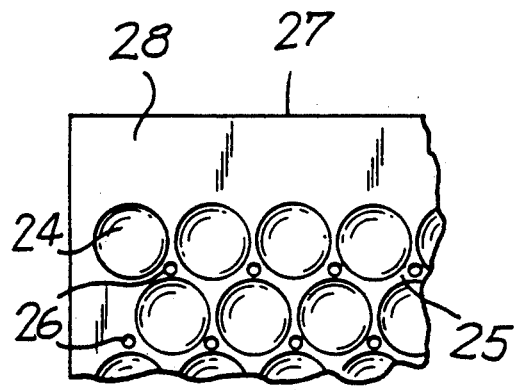
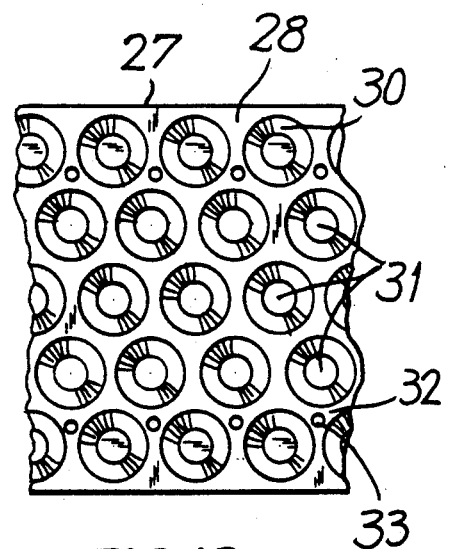
FIG.11  FIG.12

MEDICATING IMPRESSED FILM WOUND DRESSING

CROSS-REFERENCE

This is a continuation of Ser. No. 085,475 filed Aug. 13, 1987 now abandoned.

The present invention relates to low adherency wound dressings which may contain a medicament suitable for topical application to wounds, to their preparation and use.

Dressings which consist of a medicated ointment — impregnated open-work support such as tulle gras have been used for many years for dressing wounds, see for example United Kingdom Patent No. 1090421 and 1599159. A disadvantage which is found with this type of dressing is that the healing wound may, despite the presence of an ointment, grow into the tulle gras and which therefore cannot be removed without retraumatising the wound.

European Patent Application No. 171268 discloses an absorbent dressing comprising a bag formed from a film containing apertured depressions and holding pieces of foam. The construction of the film is such as to prevent re-emergence of any absorbed exudate from the dressing. This advantageous property also retards the release of medicament which may be present within the bag.

I have now found that by using a dressing which employs a film containing depressions in which the depressions are substantially full of a medicated viscous pharmaceutical carrier the above disadvantages may be mitigated. It is a feature of the prior art dressings that unimpeded transmission of exudate through the dressing to an absorbent element is permitted. The fact that my dressing satisfactorily transmits exudate is suprising since the progress of exudate would seem to be impeded by the presence of the viscous carrier which fills the depressions and covers the apertures. The dressings of the present invention further show a low propensity to adhere to the wound and effectively release the medicament from the carrier and also may provide a metered dose and a metered release rate of the medicament which is not obtainable when using medicated carriers alone.

A dressing comprising a film containing depressions has the added advantage that different types of pharmaceutically acceptable carriers may be held within the depressions whereby more than one medicament may be released to the skin surface. Antibacterial agents are particularly suitable for use in this dressing.

Accordingly the present invention provides a non-adherent wound dressing comprising a film which contains depressions over the operative area of the dressing and contained within the depressions a viscous pharmaceutically acceptable carrier.

The operative area of the dressing is that area which covers the wound and the area of skin adjacent to the wound.

However, it is preferred that the dressings of the present invention will contain within the depressions a pharmaceutically acceptable carrier containing medicament.

The medicament present in the pharmaceutically acceptable carrier may be any one of those which may be topically applied to the skin including, steroids, debriding agents, wound healing promoters, local anaesthetics, antibacterial agents, antibiotics and the like. Preferably the medicament will comprise antibacterial agent. Suitable antibacterial agents include iodophors such as polyvinyl pyrrolidone-iodine, chlorhexidine and its salts such as the diacetate, digluconate and dihydrochloride, silver compounds such as silver sulphadiazine or may comprise an admixture of two or more compatible antibacterial agents.

The amount of medicament which is applied topically may be regulated by its concentration in the carrier and by the frequency and dimensions of the depressions which hold the carrier.

The carrier will contain a therapeutically effective amount of medicament Thus for example in a preferred embodiment the carrier will comprise an ointment containing antibacterial agent at a concentration of, for example, 1 to 12.5% by weight based on the weight of the carrier.

In one embodiment the film which contains the depressions is continuous, that is does not contain apertures. Aptly the film maybe then formed from a material which has a moisture vapour transmission rate (MVTR) of greater than 250 g/m$^2$/24h at 37° C. and 100% to 10% relative humidity difference, more suitably greater than 500 g/m$^2$/24h and most suitably greater than 1000g/m$^2$/24h when measured using the Payne Cup Method. In such dressings the normal perspiration of the skin will evaporate through the film and so avoid causing maceration to the underlying skin.

The depressions containing the apertures may be arranged in a pattern within the borders of the film comprising the dressing. For example, a square dressing of 10 cm×10cm might comprise a central portion of 5cm×5 cm in which the depressions contain apertures surrounded by a border 2.5 cm wide of flat film or of a film containing unapertured depressions. Alternatively a strip of apertured depressions may extend across the width of the dressing leaving a flat film or a film containing unapertured depressions on two opposite sides.

The film used in the dressings of the present invention may be considered to have depression impressed out of the plane of the film over the operative area of the dressing. Suitably each depression may contain at least one aperture within its walls, however, it is preferred if each depression has a single aperture which may be formed for example by the removal of the apex of the depression during the manufacturing step.

The use of a film containing apertured depressions is further preferred because it is observed that exudate flows more freely to any absorbent pad used in conjunction with the dressing through the apertures thereby reducing risk of trapping exudate beneath the dressing. It is also observed that dispersal of the medicated carrier from the depressions is also facilitated.

However, in a favoured embodiment at least a portion of the depressions may each contain one or more apertures. Here the film may be formed, for example from a film which has a low moisture vapour transmission rate as such films have been observed to have an even lower propensity to adhere to the wound than have the previously mentioned moisture vapour permeable films.

Thus in a favoured aspect the present invention provides a non-adherent wound dressing comprising a film which contains a pattern of depressions therein over the operative area of the dressing and wherein at least a portion of the depressions each contain one or more apertures and contained within the depressions a viscous pharmaceutically acceptable carrier.

The film containing the depression may be considered to have a thickness defined as the perpendicular distance between the tip of the depression or the aperture and the plane of the film.

Suitably the film will have a thickness as hereinbefore defined of from 0.1 to 3 mm, more suitably 0.75 to 2 mm and preferably 1.0 to 1.5 mm.

When apertures are present then suitably the apertures in the film will have an area equivalent to a circle diameter 0.25 mm to 1.5 mm and preferably 0.3 to 1.0 mm. The open area of the apertured film may suitably be between 1 and 25% and more suitably 10 and 25%.

A contribution to the low adherency shown by the dressings of the present invention is believed to be due to the small land area between the depressions. This land area is the area in the operative area of the dressing which may contact the skin when the dressing is in place. Suitably the land area may comprise 5 to 10% of the surface of the film containing the depressions.

Suitably the number of depressions per sq. cm may be in the range from 4 to 30 per sq. cm, more suitably will be from 5 to 20 per sq. cm and preferably 6 to 12 per sq. cm.

Suitably the ratio of the land area to the area of the depressions may be in the range 1:20 to 1:9.

The land area may also contain apertures. These apertures may be suitably from 0.1 to 1.0 mm and may facilitate the flow of wound exudate from a heavily exuding wound or where the ointment is not capable of dissolving or dispensing quickly enough to cope with the evolution of exudate.

The dressings of the present invention may have adhesive coated handles along at least one of their edges for the purpose of adhering the dressing to the skin. Suitably the dressings have adhesive coated handles on two opposed edges. One advantage of using adhesive coated handles is that during the application of the dressing a handle may be adhered to the skin to stabilise the dressing and then a second or other handles may be adhered to the skin so that during wear any tendency for the dressing to move relative to the surface of the wound is reduced. Suitable handles and the material from which they may be made are described in European Patent Application No. 161865.

Aptly the dressings of the present invention are sterile and are packaged in bacteria-proof, water-proof pouches until required. The dressings may be sealed into the pouch and sterilised by conventional methods.

Alternatively the components of the dressing may be made separately in a sterile condition and assembled under sterile conditions and then sealed into a pre-sterilised bacteria-proof, water-proof pouch. Suitable pouches include one available as 's b w' View Pack (Trade Mark) and vacuum formed styrene trays with foil or styrene lids.

The pharmaceutically acceptable carrier may be bland that is it may not contain any medicament, for example, it may comprise an emollient cream but preferably the carrier will contain medicament The pharmaceutically acceptable carrier is present in individual depressions within the film. It is therefore possible to employ more than one carrier to carry more than one medicament in a single dressing. The carriers may be spread in a pattern so that the two carriers are mutually non-overlapping. Alternatively two medicaments could be combined in one carrier. It is also possible to contain one medicament within two different carriers which provided different release rates for the medicament, for example one carrier may give rapid release and one may give sustained release.

A film containing depressions but not apertures may be prepared by placing a strip of the film onto an embossed film of polypropylene having a regular pattern of embossments. The two films are passed in contact between the nip of two rollers under pressure. The rollers comprise a silicone rubber coated roller and a metal roller heated to elevated temperature, for example 80° to 100° C., depending upon the nature of the film. The film is retrieved as a film containing depressions impressed out of the plane of the film. The film may be made from an ethylene-vinyl acetate copolymer-styrene incompatible blend or from moisture vapour permeable material such as a hydrophilic polymer for example a hydrophilic polyurethane.

A film containing apertures in the depressions may be prepared by placing a polymer film on to the embossed surface of a thermoplastic polymeric film. The embossments are suitably arranged in a pattern and are in the form of discrete, raised areas with troughs between them. The embossment may be any shape including square truncated pyramidal, hexagonal, conical or hemispherical. A film of polyethylene is placed over the polymer film urging it against the embossments. The three layered sandwich is then subjected to pressure at elevated temperature, for example 80° C. for a period of time. The temperature, pressure and time required for the process will depend upon the properties of the polymer film but will be sufficient for the film to flow away from the tip of the embossment leaving the tops of the embossments uncovered so forming the aperture in the depression in the film. The pressure and heat are discontinued and the polyethylene film is removed. The apertures which are uppermost may be covered by a sheet of polyester film which is then adhered lightly to the film surrounding the apertures by a heated iron. The film containing the apertured depressions and polyester film may then be peeled from the embossed thermoplastic polymeric film. The depressions in the film may then be filled with the medicament in its carrier. The embossments of the thermoplastic film may be pretreated with a release compound to facilitate release of the film containing the depressions. In a preferred form the film has geometrically shaped depressions having approximately circular holes at their apex.

Polymeric material which is suitable for preparing films containing the depressions include thermoplastic elastomeric polymers or polymer blends. A favoured polymeric material is a blend of an ethylene-vinyl acetate copolymer and an incompatible polymer such as a polyolefin and particularly polystyrene. A particularly preferred polymeric material is a blend of from 40 to 90 parts by weight of ethylene-vinyl acetate copolymer and 60 to 10 parts by weight of polystyrene and more preferably 60 to 90 parts ethylene-vinyl acetate copolymer and 40 to 10 parts polystyrene. If necessary the polymeric material may include fillers or whitening materials such as titanium dioxide.

The film from which the film containing depressions is formed may suitably have a thickness of from 50 $\mu$m to 120 $\mu$m and preferably 75 to 100 $\mu$m.

In an alternative embodiment of the present invention the apertures in the depressions of the film may be covered by a polypropylene film which ma be vacuum formed onto the apertured film whilst it is still in place on the embossed polypropylene film The apertured film and the polypropylene film may be peeled away from the polypropylene embossed film. The depressions are filled by the carrier in the method hereinafter described and a release paper placed over the carrier.

The medicament when in the dressings of the present invention may be in the form of a pharmaceutical composition which is suitable for topical treatment of skin or wounds for example treatment of burns, ulcers and other skin lesions exposed to the risk of infection. Suitable forms of the topical composition of this invention include ointments, gels, oily suspensions, emulsions, lotions, pastes, powders and the like which are viscous enough to be retained in the depressions in the film.

Preferably the composition will be in the form of an ointment and most preferably as a hydrophilic ointment such as an oil-in-water emulsion. Suitable bases are described in Chapter 87 Ointments:Emulsion Bases in Remingtons Pharmaceutical Sciences, 15th Ed 1975, pages 1532–34. Other suitable ointment bases include those described in British Patent No. 1240545

A particularly suitable ointment base is therefore an oil-in-water emulsion containing from 0 to 25% of petrolatum or liquid paraffin, 2 to 20% of a fatty alcohol, 0 to 12% of an emulsifying agent, up to 10% of non-ionic surfactant and 5 to 25% of a polyhydric alcohol and the balance to 100% being deionised or distilled water. Aptly the fatty alcohols are those conventionally used in ointments and are water insoluble. Suitable alcohols include stearyl alcohol, cetyl alcohol, lauryl alcohol and myristyl alcohol. Suitably the emulsifying agent is a glyceryl fatty acid ester and is preferably glyceryl monostearate. Suitable non-ionic surfactants include the polyoxyethylated sorbitan fatty acid esters and sorbitan fatty acid esters. An emulsifying wax may be used in place of both or part of both of the fatty alcohol and non-ionic surfactant. The polyhydric alcohol acts as a humectant and suitable alcohols include propylene glycol, sorbitol or glycerin or mixtures thereof.

An alternative ointment may contain one or a mixture of polyalkylene glycols for example polyethylene glycol. Suitably the ointment may contain a mixture of a high molecular weight polyethylene glycol and a low molecular weight polyethylene glycol.

The compositions used in the present invention may be in the form of an aqueous gel. Suitable gelling agents include polyoxyethylene-polyoxypropylene diol block copolymers, polyacrylic acid lightly cross-linked with triallyl sucrose which has been neutralised using an alkali metal hydroxide, cellulosic derivatives such as carboxymethyl cellulose, hydroxymethyl cellulose, natural gums and the like. A preferred group of gelling agents are the polyoxyethylene-polyoxypropylene diol block copolymers which are commercially available as the Pluronics from BASF-Wyandotte. (Pluronic is a registered trade mark of BASF-Wyandotte).

Suitable gel forming block copolymers of polyoxyethylene-polyoxypropylene will have a molecular weight from 4,600 to 13,500 (approximately) and will be present in the gel in an amount from 50% for the lower molecular weight copolymers to 20% for the higher molecular weight copolymers, so that the gel when applied topically is neither too stiff nor too fluid. Typically the gels are formed by mixing together the copolymer and water to form an aqueous solution at a temperature of 2° C. and adding the medicament and then allowing the solution to gel as it warms to ambient temperature. Suitable Pluronics are those designated as F108, F127 and P105.

The composition used in the present invention may also be in the form of a hydrophobic ointment. Suitable hydrophobic ointments are those which are formed from white or yellow soft paraffin or a mixture of such with liquid paraffin. A preferred ointment base comprises a mixture of white soft paraffin and liquid paraffin in a ratio of 5:1 to 1:1. However, in general terms aqueous based systems will be preferred.

The hydrophobic ointment base may also contain non-ionic surfactants such as polyoxyethylated sorbitan fatty acid esters and sorbitan fatty acid esters. The presence of non-ionic surfactants increases the miscibility of the ointment with wound fluid and aids release of the medicament. Suitably the non-ionic surfactant will be present in an amount from 0.1 to 0.5%. Preferably the non-ionic surfactant is 0.1% of polyoxyethylene sorbitan triolate and 0.1% sorbitan monopalmitate.

The pharmaceutically acceptable carrier may be placed in the depressions in the film by spreading it over the film using a doctor blade and removing any excess. The carrier substantially fills the depressions and the polyester film or vacuum-formed polypropylene film covering the apertures prevents the pharmaceutical composition passing through the apertures. The other side of the apertured film may then be covered by a piece of paper or film which forms a protector during storage. In use the dressing is removed from the pouch, the protector is removed and the dressing placed with the pharmaceutically acceptable carrier against the skin. The polyester film or polypropylene film covering the apertures is then removed. The dressing may be held in place by conventional bandage means. Aptly an absorbent pad may be placed over the apertures to absorb any exudate which might issue from the wound.

Aptly the dressings of the present invention are sterile and are packaged in bacteria-proof, water-proof pouches until required. The dressings may be sealed into the pouch and sterilised by conventional methods.

In a further aspect therefore the present invention comprises a method of treatment which comprises applying to the body of an animal a dressing as hereinbefore described.

Preferred embodiments of dressings of the invention will now be described by way of example only and with reference to the drawings in which FIG. 1 shows a dressing comprising a continuous film containing depressions within a boarder of flat film.

FIG. 2 shows a cross-section through the dressing of FIG. 1.

FIG. 3 shows a dressing comprising a film containing square pyramidal depressions which are apertured.

FIG. 4 shows a cross-section through a portion of the dressing of FIG. 3.

FIG. 5 shows a dressing comprising a film containing conical depressions the inner rows which are apertured and the outer rows which are continuous.

FIG. 6 shows a cross-section through the dressing of FIG. 5.

FIGS. 7 and 9 show a dressing comprising a continuous film with alternative patterns of depressions.

FIGS. 8 and 10 show a cross-section through a portion of the dressings shown in FIGS. 7 and 9 respectively.

FIGS. 11 and 12 show magnified portions of dressings of the type shown in FIGS. 1 and 5 respectively in which the land area between the depressions contains apertures.

The dressing illustrated in FIG. 1 shows a dressing (1) formed from a continuous film (2) which contains a pattern of depressions (3) in the form of a strip which lies in the centre of the dressing (1) and is the operative area of the dressing The film is formed from a moisture vapour permeable material such as a polyurethane, for example an Estane (Trade mark), an elastomeric polyester, for example a Hytrel (Trade mark) and a polyetherpolyamide for example a Pebax (Trade mark). A preferred film may be prepared from a hydrophilic polymer such as a hydrophilic polyurethane which aptly contains from 20 to 40% by weight of water when hydrated. Suitable hydrophilic polyurethanes are described in United Kingdom Pat. No. 2093190B.

The film (4) which surrounds the depressions (3) is flat and could carry a coating of a skin-compatible pressure-sensitive adhesive for adhering the dressing to the skin. The pharmaceutically acceptable carrier is contained within the depressions (3).

FIG. 2 shows a cross-section through the dressing shown in FIG. 1 along the line 2—2. The figure shows the relatively small amount of land area (5) between the depressions (3). Only a small amount of this area (5) would contact the skin over the wound and hence the dressing shows lo wound adherency.

FIG. 3 shows a second embodiment of a dressing of the present invention. The dressing (6) comprises a film (7) which contains depressions (8) in the form of square pyramids the apices of which have been removed during their preparation. In this embodiment the film is completely covered by depressions. The pharmaceutically acceptable carrier (9) may be placed in any or all of the depressions (8). Prior to use the dressing is sandwiched between two removable protector layers (not shown) to prevent the carrier being ejected from the depressions for example during transportation or storage. The film is suitably formed from a blend of ethylene-vinyl acetate copolymer and polystyrene.

FIG. 4 shows a cross-section through a portion of a dressing shown in FIG. 3. The depressions (8) are caused to contain apertures (10) by removing the apices of the square pyramids in the forming process. The pharmaceutically acceptable carrier (9) is placed in the depressions (8). The land area (11) between the depressions (8) forms from 5 to 10% of the area of the film.

FIG. 5 shows a third embodiment of a dressing of the present invention. The dressing (12) comprises a film (13) which contains a pattern of conical depressions (14). In this dressing the two outer rows of the depressions (14) are not apertured while the inner rows contain an aperture (15) formed by removal of the apices of the cone during manufacture.

FIG. 6 shows a cross-section through a dressing shown in FIG. 5 along the line 6—6. The outer two rows of depressions (14) are not apertured while the centre three rows are apertured.

FIGS. 7 and 9 show dressings (16, 19) which comprise a continuous film (17, 20) which has different types of depressions (18, 21) impressed in the film. FIGS. 8 and 10 show the corresponding cross-section views of the dressings 7 and 9.

FIG. 11 shows a magnified section of the type of dressing shown in FIG. 1 which comprises a dressing (22) formed from a continuous film (23) having depressions (24) impressed out of the plane of the film. The land areas (25) contain small perforations (26) which permit transmission of wound exudate from heavily exuding wounds.

FIG. 12 shows a magnified section of the type of dressing shown in FIG. 5 which comprises a dressing (27) formed from a film (28) having conical depressions (29) the outer rows (30) of which are not apertured and the inner rows (31) which are apertured. The land areas (32) contain apertures (33) close to the non-apertured depressions (30).

EXAMPLE 1

A film was prepared by extruding a blend of ethylene-vinyl acetate copolymer (80 parts by weight), high impact polystyrene (20 parts by weight) and titanium dioxide (4% by weight of the weight of polymers). The film had a thickness of 75 to 100 $\mu$m. A strip of the film was placed on an embossed film of polypropylene having hexagonal bosses arranged so that there are 10 embossments per sq.cm. (approx). The two films were passed in contact between the nip of two rollers under pressure, a silicone rubber coated roller and a metal roller heated to 100° C. with a silicone rubber mat being in contact with the other side of the blend film. A second pass was made between a silicone rubber roller and a metal roller at 100° c. to form the apertures, (if a non-apertured film is required this second pass will be omitted), whereby the excess polymer blend material from the apertures is removed on the metal roller. The embossed apertured polymer blend film was then removed from the polypropylene embossed film and then re-applied. A film of polyester was lightly adhered to the blend film over the apertures using pressure and heat. The embossed apertured film — polyester laminate was then recovered from the polypropylene embossed film to provide the laminate of embossed apertured film containg depressions adhered to a polyester film which contacted and covered the apertures of the film.

An ointment comprising 1% silver sulphadiazine in a hydrophilic ointment was spread over the polymer blend film dressing so that the ointment entered into the depression. Any excess ointment was removed by scraping the surface with a flat blade. The presence of the polyester film prevents the ointment from running out through the apertures. The dressing may be covered by a second releaseable layer and packaged in a bacteria proof, water-proof pack and sterilised by 2.5 Mrad gamma-irradiation.

EXAMPLE 2

A film was prepared by extruding a blend of ethylene-vinyl acetate copolymer (90 parts by weight), high impact polystyrene (10 parts by weight) and titanium dioxide (4% by weight of the weight of polymers). The film had a thickness of 80 $\mu$m. A strip of the film was placed on an embossed film of polypropylene having hexagonal embossment arranged so that there are 10 embossments per sq.cm. The two films were passed in contact between the nip of two rollers under pressure, a silicone rubber coated roller and a metal roller heated to 100° C. A rigid, plain film of polyethylene was then placed onto the polymer blend film and a second pass was made between the nip of two metal rollers heated to 100° C. The film sandwich was allowed to cool and the polyethylene film removed. A film of polyester (Melinex, trade mark) was lightly adhered to the embossed film over the apertures using pressure and heat. The embossed polymer blend film was then removed from the polyethylene embossed film, to provide a laminate of embossed polymer blend film adhered to a polyester film which contacted and covered the apertures of the embossed film.

An ointment was prepared by mixing together polyethylene glycol 400 (70 parts by weight), polyethylene glycol 4000 (20 parts by weight) and polyvinyl pyrrolidone — iodine (10 parts by weight)

The ointment was spread over the polymer blend embossed film dressing so that the ointment was filled into the depressions. Any excess ointment was removed by scraping the surface with a flat blade. The presence of the polyester film prevents the ointment from running out through the apertures. The dressing may be covered by a second releasable layer and packaged in a bacteria proof, water-proof pack and sterilised by gamma-irradiation.

In use the dressing is removed from the pack and the first release layer removed, the dressing is then placed with the ointment against the skin and the polyester film is removed. An absorbent pad may be placed onto the dressing in contact with the apertures.

EXAMPLE 3

A polymer blend film was embossed in a similar manner to that described in Example 1. Instead of using a polyester film, a polypropylene film was vacuum formed over the embossed film to cover the apertures. The laminate could be peeled from the polyethylene embossed film because the polymer blend film adhered more strongly to the polypropylene than to the polyethylene. The ointment was then filled into the depressions as before in Example 1 and the dressing packaged an sterilised as previously.

In use the dressing was placed against the skin and the vacuum formed polypropylene peeled off.

EXAMPLE 4

A dressing similar to that described in Example 1 was prepared except that the ointment was formed from an oil-in-water emulsion containing silver sulphadiazine.

EXAMPLE 5

A dressing similar to that described in Example 1 was prepared except that the ointment was formed from an oil-in-water emulsion containing chlorhexidine di gluconate or chlorhexidine diacetate.

EXAMPLE 6

A film of a thermoplastic polyurethane, Estane 5714F, is placed against an embossed film of polypropylene. The two films are passed on contact between the nip of two rollers under pressure and at an elevated temperature. Depressions are formed in the polyurethane film without creating apertures. The film is removed from the embossments and an oil-in-water composition containing silver sulphadiazine is filled into the depressions and covered by a removable protector. The dressing so formed may be placed in a vacuum formed styrene tray and covered with a foil lid and sterilised.

EXAMPLE 7

A dressing similar to that described in Example 6 is prepared except that the film used is a polyetherpolyester elastomer, Hytrel 4056 and the composition comprises 10% polyvinyl pyrrolidone-iodine in a polyethylene glycol carrier.

EXAMPLE 8

A dressing similar to that describd in Example 6 is prepared using a hydrophilic polyurethane prepared in manner described in Example 2 of United Kingdom Pat. No. 2093190B. The depressions are filled with a hydrophobic ointment composition containing chlorhexidine digluconate and a surfactant.

I claim:

1. A non-adherent dressing comprising a film which contains depressions impressed out of the plane of the film over the operative area of the dressing and flat land areas between the depressions, wherein at least a portion of the depressions contain one or more apertures, which land area may contact the skin when the dressing is in place and a viscous pharmaceutically acceptable carrier contained within the depressions.

2. A wound dressing according to claim 1 in which the pharmaceutically acceptable carrier contains a therapeutically effective amount of at least one medicament.

3. A wound dressing according to claim 2 in which the pharmaceutically acceptable carrier contains from 1 to 12.5% of antibacterial agent.

4. A wound dressing according to claim 3 in which the antibacterial agent comprises silver sulphadiazine.

5. A wound dressing according to claim 3 in which the antibacterial agent comprises of polyvinyl pyrrolidone-iodine.

6. A wound dressing according to claim 3 in which the antibacterial agent comprises a salt of chlorhexidine.

7. A wound dressing according to claim 1 in which the film which contains the depressions is continuous and has a moisture vapour transmission rate of greater than 250 $gm^{-1} 24h^{-1}$ at 37° C. and 100% to 10% relative humidity difference.

8. A wound dressing according to claim 1 in which the film contains a pattern of apertured and continuous depressions.

9. A wound dressing according to claim 1 in which each depression has an aperture at its apex.

10. A wound dressing according to claim 1 in which the apertures have an area equivalent to a circle of diameter 0.25 mm to 1.5 mm and film has an open area of between 10 and 25%.

11. A wound dressing according to claim 1 in which the land area between the depressions comprises from 5 to 10% of the surface of the film containing the depressions.

12. A wound dressing according to claim 1 in which the film is formed from a blend of ethylene-vinyl acetate copolymer and polystyrene.

13. A wound dressing according to claim 1 in which the viscous pharmaceutically acceptable carrier is an oil-in-water emulsion.

14. A wound dressing according to claim 1 in which the viscous pharmaceutically acceptable carrier is an aqueous gel.

15. A wound dressing according to claim 1 in which the viscous pharmaceutically acceptable carrier is a hydrophobic ointment.

16. A wound dressing according to claim 1 which is sterile and is packaged in a bacteria-proof and water-proof pack.

17. A wound dressing according to claim 1 in which the thickness of the film which contains depressions is from 0.1 to 3mm.

18. A wound dressing according to claim 1 in which the film contains from 4 to 30 depressions per square centimeter.

19. A wound dressing according to claim 1 in which ratio of the land area to the area of depressions is 1:20 to 1:9.

20. A wound dressing according to claim 1 in which the land area also contains apertures which may be from 0.1 to 1.0 mm in diameter.

21. A wound dressing according to claim 1 in which the viscous pharmaceutically acceptable carrier is a hydrophilic ointment.

22. A non-adherent wound dressing comprising a film which contains depressions impressed out of the plane of the film over the operative area of the dressing and a viscous pharmaceutically acceptable carrier contained with the depressions wherein at least a portion of the depressions contain one or more apertures, wherein the film carries along at least one edge an adhesive coated handle capable of adhering to the skin.

23. A wound dressing according to claim 22 in which the dressing carries adhesive coated handles along two opposed edges.

24. A non-adherent wound dressing comprising a film which contains depressions impressed out of the plane of the film over the operative area of the dressing and flat land area between the depressions, wherein at least a portion of the depressions contain one or more apertures, which land area may contact the skin when the dressing is in place and a viscous pharmaceutically acceptable carrier containing a therapeutically effective amount of at least one medicament, contained within the depressions, wherein the pharmaceutically acceptable carrier is a hydrophilic ointment, the medicament is polyvinylpyrrolidone-iodine and the film is a blend of ethylene-vinyl acetate copolymer and polystyrene.

25. A method of treatment of a wound which method comprises applying to the wound a dressing comprising a film which contains depressions impressed out of the plane of the film over the operative area of the dressing and a viscous pharmaceutically acceptable carrier contained within the depressions wherein at least a portion of the depressions contain one or more apertures, wherein the film carries along at least one edge an adhesive coated handle capable of adhering to the skin.

26. A method of treatment according to claim 25 in which the viscous pharmaceutically acceptable carrier contains from 1 to 12.5% of antibacterial agent.

* * * * *